US005470874A

United States Patent [19]
Lerner

[11] Patent Number: 5,470,874
[45] Date of Patent: Nov. 28, 1995

[54] ASCORBIC ACID AND PROANTHOCYANIDINE COMPOSITION FOR TOPICAL APPLICATION TO HUMAN SKIN

[76] Inventor: Sheldon Lerner, 3399 First Ave., San Diego, Calif. 92103

[21] Appl. No.: 323,095

[22] Filed: Oct. 14, 1994

[51] Int. Cl.$^6$ .............. A61K 6/00; A61K 31/34; A61K 31/355

[52] U.S. Cl. .............. 514/474; 424/59; 424/60; 424/195.1; 424/196.1; 514/54; 514/56; 514/453

[58] Field of Search .............. 424/59, 60, 195.1, 424/196.1; 514/54, 56, 453, 474

[56] References Cited

U.S. PATENT DOCUMENTS

| | | | |
|---|---|---|---|
| 4,424,232 | 1/1984 | Parkinson | 424/319 |
| 4,588,590 | 5/1986 | Bernstein | 424/195.1 |
| 4,668,516 | 5/1987 | Duraffourd et al. | 424/195.1 |
| 4,707,354 | 11/1987 | Garlen et al. | 424/59 |
| 4,822,816 | 4/1989 | Markham | 514/474 |
| 4,863,956 | 9/1989 | Gabetta et al. | 514/453 |
| 4,888,354 | 12/1989 | Chang et al. | 514/343 |
| 4,925,870 | 5/1990 | Gabetta et al. | 514/453 |
| 4,925,871 | 5/1990 | Gabetta et al. | 514/453 |
| 4,938,960 | 7/1990 | Ismail | 514/548 |
| 4,938,969 | 7/1990 | Schinitsky et al. | 514/847 |
| 4,963,527 | 10/1990 | Bombardelli et al. | 514/25 |
| 4,983,382 | 1/1991 | Wilmott et al. | 514/474 |
| 5,021,452 | 6/1991 | Labbé et al. | 514/474 |
| 5,032,610 | 7/1991 | Borretzen et al. | 514/467 |
| 5,122,536 | 6/1992 | Perricone | 514/474 |
| 5,135,948 | 8/1992 | Borretzen et al. | 514/467 |
| 5,140,043 | 8/1992 | Darr et al. | 514/474 |
| 5,198,465 | 3/1993 | Dioguardi | 514/474 |
| 5,298,237 | 3/1994 | Fine | 514/944 |
| 5,308,621 | 5/1994 | Taylor et al. | 424/401 |
| 5,360,824 | 11/1994 | Baker | 514/474 |
| 5,371,107 | 12/1994 | Hotzel et al. | 514/474 |
| 5,409,693 | 4/1995 | Perricone | 514/474 |

Primary Examiner—Ronald W. Griffin
Attorney, Agent, or Firm—Linda R. Neyenesch

[57] ABSTRACT

A method and composition for topically administering ascorbic acid and proanthocyanidine for application to human skin care. The substance is composed of 10% to 25% ascorbic acid and at least 0.5% to 5% proanthocyanidine in combination with a high ratio water surfactant. Non-irritating thickeners, preservatives and carriers synergize to allow penetration of a serum composition to access the entire dermal membrane. The composition possesses sunscreen properties and superior collagen repair means.

18 Claims, No Drawings

ASCORBIC ACID AND PROANTHOCYANIDINE COMPOSITION FOR TOPICAL APPLICATION TO HUMAN SKIN

BACKGROUND OF THE INVENTION

1. Field of the Invention

The present invention relates to a vitamin C (ascorbic acid) composition and methodology for topical application to human skin. The invention comprises a serum which penetrates dermal layers which affect collagen formation and improvement, thus achieving healthy, smooth and clear skin throughout the entire dermal membrane. This major improvement of topical application has been facilitated by an appropriately balanced pH composition which is easily absorbed by the dermis. Topical application of the composition also provides ultraviolet protection, a new and useful improvement of the application of ascorbic acid without the disadvantageous side affects associated with oral administration. Research has repeatedly confirmed toxic levels and adverse side effects in human subjects amounting to overdose pathology in attempts to achieve sunscreen properties now possible with applicant's topical composition.

A secondary embodiment of the invention combines ascorbic acid and proanthocyanidine to achieve synergy and exponential effectiveness of the free radical scavenging effects of both substances.

2. Prior Art

Applicant conducted national and international searches in the fields of topical application of ascorbic acid and proanthocyanidine. Although the benefits of oral and/or intravenous administration are present in the prior art and numerous publications, topical application is an entirely new field of art, especially with respect to the composition claimed.

For example, the reference to Markham (U.S. Pat. No. 4,822,816) refers to oral administration. This patent acknowledges ascorbic acid's excellent free radical scavenging attributes, as well as enzyme reactions which enhance formation of collagen. Markham's two claims set forth a composition which alleges improved oral absorption qualities.

The present invention has reduced to practice a novel composition which harnesses ascorbic acid as well as proanthocyanidine in a serum medium of pH compatibility suitable or topical application to achieve unprecedented improvement in the field of skin care, as will be described.

SUMMARY OF THE INVENTION

This invention is directed to the treatment of physiologic conditions commonly associated with the pathology of a wide range of skin disorders, the treatment comprising stimulation of collagen synthesis and therefore repair of impaired collagen. From the etiology of collagen repair flows morphological improvement throughout the entire dermal membrane of striking results. Visible wrinkles, leatheriness, roughness, dryness, skin looseness, loss of elasticity and pigment variations such as acne are mitigated or entirely vanish, depending upon the severity of the condition.

The invention comprises a mixture of free radical scavengers embodied in ascorbic acid and proanthocyanidin. This composition is stabilized in a serum of superior bioavailability relative to topical application. The free radical scavenging effects of the serum neutralize unstable oxygen molecules which degrade collagen.

Discussion of the attributes of the primary compounds are essential to the novelty of this invention inasmuch as nowhere in the prior art has a composition of such compatibility and effectiveness been achieved for topical application. Therefore, the benefits of oral application will begin with ascorbic acid.

Extrapolation to the benefits of topical application will become apparent from the respective discussions of each compound.

Higher primates, including humans, cannot produce ascorbic acid. Historically, precursor societies acquired Vitamin C through hunting and gathering of food rich in ascorbic acid. With the exception of ultraviolet radiation (although now more dangerous due to Ozone depletion), these societies existed in a world unlike today. Pollution, cigarette smoke, toxic waste, polluted water, polynuclear waste, and an infinite cast of pollutants and physiologic stressors combine to affect global environments. Urban societies suffer higher stress levels than rural populations. All of these factors stress human physiology and drain its Vitamin C. These negative environmental conditions are unprecedented in human evolution.

What does Vitamin C do for human physiology? It protects the brain and spinal cord from free radicals. It promotes collagen (connective tissue) synthesis, in lipid (fat) and carbohydrate metabolism, and the manufacture of neurotransmitters. It is also essential for optimum maintenance of the immune system. Vitamin C is toxic to a wide range of cancer cells, especially melanoma. The oxidizing enzyme tyrosine that catalyzes the aerobic action of tyrosine into melanin and other pigments is also inhibited by the presence of Vitamin C. Vitamin C has been found to be effective in catalyzing the immune response to many viral and bacterial infections. Besides the many applicable uses set forth above, Vitamin C is essential for collagen synthesis and wound healing.

Relevance of topical application to the instant invention is especially pertinent with respect to ultraviolet protection, melanoma, collagen synthesis and protection against damaging chemicals associated with cigarette smoking, i.e., nicotine, carbon monoxide, N-nitrous compounds, NOx (nitrogen oxides, nitric acid gas), cadmium and polynuclear aromatic hydrocarbons. Vitamin C is depleted in its free radical scavenger capacity while destroying these noxious substances.

Proanthocyanidins comprise the second compound. These substances are derived from non-toxic pine bark, a widely available and cost-effective component. Proanthocyanidins fall within the plant polyphenols and are characterized by superior free radical scavenging effects, bioavailibility and lack of toxicity. Although the traditional method of administration has been oral or intravenous, the pertinent application to the present invention is the prevention and/or repair of collagen tissue.

Yet another aspect of the invention is evidence that the stratified human epidermis displays a coordinated response from growth factor signaling pathways generated low in the basal membrane of the dermis.

Applicant's novel combination of superior radical scavengers in combination with pH skin compatibility therefore achieves bioavailabilty with topical application. This catalyst comprises a molecular signal for cell proliferation as well as ultraviolet protection.

The clinical evidence which follows reveals enhanced tissue healing response time. Absence of irritating side effects such as burning or allergic response is yet another advantage of the invention which therefore allows liberal application of the composition.

Yet another object of the invention is its tolerance for temperature variations and long shelf-life.

A further object of the invention is its economy of manufacture and availability and reasonable cost to the consumer.

DETAILED DESCRIPTION OF THE INVENTION

The therapeutic components of the ascorbic acid and pranthocyanidine compounds are described below:

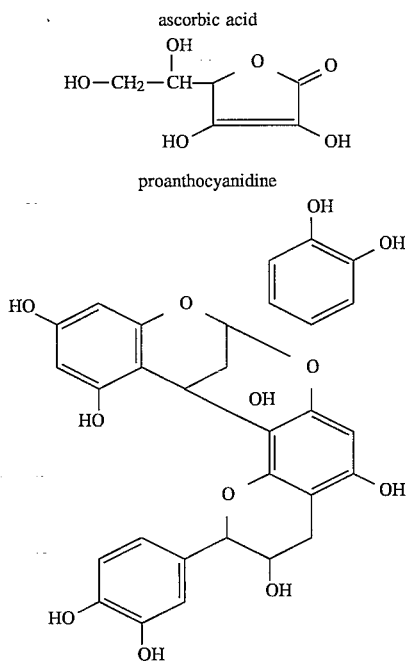

The limitations of oral or intravenous treatment with the above compounds have been discussed with respect to the attributes. Essential to the detailed description is the composition of the serum.

Without limiting the scope of the invention and for purposes of illustration, the aqueous base composition of the invention for topical application to human skin is described as follows.

In the first embodiment, ascorbic acid (10% to 25%) has been found to be effective when carried by a water surfactant (surfaceacting agent) in the approximate solution of 30% to 90%. This high water to ascorbic acid proportion is effective inasmuch as the water easily penetrates the dermis, evaporates, and leaves the nutrient deep within the dermal membrane for optimal bioavailability. Methylparaben is included in the approximate range of 3% to 10%; Propylparaben is also included in the approximate range of 0.1% to 0.3%, both comprising preservatives. Sodium hydroxide is also utilized in trace amounts as a preservative. Propylene glycol (a colorless, viscous, hygroscopic liquid) is included as a thickener and gives integrity to the serum composition in the approximate range of 1% to 3%. Xanthum gum occurs in the approximate amount of 1% as a buffer and neutral pH adjuster. Hyaluronic acid (a mucopolysaccharide) is included in the range of 0.1% to 0.3% and enhances lubricating qualities of the serum. Ascorbic palmitate comprises an ester of palmitic acid present in the approximate range of 1%. Trace elements of diazolidnyl urea (0.1% or less) enhance the moisture retention qualities of the serum. Trace elements of Thretonate (0.1% or less) facilitate uptake of the composition in a metabolite capacity. Last but not least is 0.1% of tetasodium EDTA, a preservative.

The second embodiment of the invention includes the pine bark extract known as proanthocyanidine, also known as pycnogenol. This substance has been found most effective in combination with ascorbic acid in the approximate amount of 1% to 5%, although this substance may be used in liberal amounts in view of its non-toxicity. Ascorbic acid (10% to 25%) and proanthocyanidine have been found to be effective when carried by a water surfactant (surface-acting agent) in the approximate solution of 30% to 90%. This high water to ascorbic acid proportion is effective inasmuch as the water easily penetrates the dermis, evaporates, and leaves the nutrient deep within the dermal membrane for optimal bioavailability. Methylparaben is included in the approximate range of 3% to 10%; Propylparaben is also included in the approximate range of 0.1% to 0.3%, both comprising preservatives. Sodium hydroxide is also utilized in trace amounts as a preservative. Propylene glycol (a colorless, viscous, hygroscopic liquid) is included as a thickener and gives integrity to the serum composition in the approximate range of 1% to 3%. Xanthum gum occurs in the approximate amount of 1% as a buffer and neutral Ph adjuster. Hyaluronic acid (a mucopolysaccharide) is included in the range of 0.1% to 0.3% and enhances lubricating qualities of the serum. Ascorbic palmitate comprises an ester of palmitic acid diazolidnyl urea (0.1% or less) enhance the moisture retention qualities of the serum. Trace elements of Thretonate (0.1% or less) facilitate uptake of the composition in a metabolite capacity. Last but not least is 0.1% of tetasodium EDTA, a preservative. As stated hereinbefore, combination of the pine bark extract with ascorbic acid achieves optimal free radical scavenging effects.

Topical application of both embodiments achieves rejuvenation and healing of the total dermal organ without adverse side effects. Applicant's clinical evidence suggests the state of the art healing time of pathological disorders of the skin. The results are exhibited by safe and expeditious exfoliation of dead, cornified layers, repair of fibroblast tissue, repair, thickening and proliferation of new cell layers, as well as increased blood flow.

The composition has proved effective with varying skin types of pigment and oil production. Because of its non-irritating qualities, the substance does not require monitoring or prescription. The human research subjects used the composition liberally with different cleansers and moisturizers. These experiments are in progress and continue to yield positive and expedient results.

EXPERIMENT PROTOCOL

Fifty patients between the ages of thirty-five and sixty applied the composition for a period of three to nine months.

EXAMPLE 1

Twenty-five subjects used the composition in conjunction with glycolic skin products. Research subjects cleansed with 4% glycolic cleanser and 8% glycolic astringent, then applied the composition and moisturized with 10% glycolic lotion. This procedure was performed twice daily, once in the morning and once in the evening.

At the end of only three months, 74% exhibited overall improvement in the clarity of skin smoothness and improved firmness. At the end of six months 84% exhibited further improvement in skin clarity, smoothness, firmness and clearly visible reduction in fine and moderate wrinkles.

At the end of nine months 88% exhibited improvement in clarity of skin smoothness and all had further or additional improvement in firmness with further reduction in fine, moderate and even deep furrows. The remaining 12% indicated deviation from the experiment protocol but did notice significant improvement.

EXAMPLE 2

Twenty-five subjects used the composition in conjunction with non-glycolic cleansers and moisturizers. As in Example 1, subjects cleansed the skin and applied the composition, after which a moisturizer was applied. Applications were made twice daily; once in the morning and once in the evening.

At the end of three months 68% exhibited improved skin firmness with degrees of improvement in skin smoothness and minimal change in skin clarity.

At the end of six months 84% exhibited further improvement in skin firmness with clearly visible reduction in fine and moderate wrinkles. The same improvement in skin smoothness and clarity was also observed as in Example 1.

At the end of nine months 86% exhibited additional improvement in skin firmness with further reduction in fine, moderate and deep furrows. The remaining 14% indicated deviation from the experiment protocol. The clinical results indicate the effectiveness of the composition with or without glycolic products, i.e., 88% visa vis 86% improvement within a relatively short period of time.

This research has been conducted without facial peels, surgery or any other clinical application than that stated in the protocol, and has achieved comparable results. The observance of collagen improvement was clearly evident, as reflected in skin health, firmness, smoothness and clarity.

Applicant has not only perfected a topical composition of superior quality, but also one that is affordable to the general public.

While there have been shown and described the preferred embodiments of the composition and its application, it will be appreciated that changes and alterations may be made therein without departing from the spirit and scope of the invention.

What is claimed is:

1. A topically applied composition of ascorbic acid for repairing and stimulating the growth of human skin comprising:

at least 10% to 25% ascorbic acid;
   at least 30% but not more than 90% water;
   at least 10% methylparaben;
   at least 0.3% propylparaben;
   at least 0.1% sodium hydroxide;
   at least 3% propylene glycol;
   at least 1% xanthum gum;
   at least 0.3% hyaluronic acid;
   at least 1% ascorbic palmitate;
   0.1% or less diazolidinyl urea;
   0.1% or less thretonate; and
   0.1% or less tetrasodium EDTA.

2. The composition of claim 1 wherein the ascorbic acid stimulates collagen synthesis.

3. The composition of claim 1 wherein the ascorbic acid provides sunscreen protection.

4. The composition of claim 1 wherein the water serves as a surfactant carrier of the composition into the dermal membrane of human skin.

5. The composition of claim 1 wherein the substances methylparaben, propylparaben, sodium hydroxide and tetrasodium EDTA provide preservative means.

6. The composition of claim 1 wherein propylene glycol serves as a thickening agent; xanthum gum provides a buffer and pH adjuster; hyaluronic acid constitutes a lubricating agent; diazolidinyl urea enhances moisture retention qualities of the composition; and thretonate enhances metabolite uptake of the composition.

7. A topically applied composition of ascorbic acid in combination with proanthocyanidines (pine tree bark extract) for repairing and stimulating the growth of human skin comprising:

at least 10% to 25% ascorbic acid;
   at least 0.5% to 5% proanthocyanidine;
   at least 30% but not more than 90% water;
   at least 10% methylparaben;
   at least 0.3% propylparaben;
   at least 0.1% sodium hydroxide;
   at least 3% propylene glycol;
   at least 1% xanthum gum;
   at least 0.3% hyaluronic acid;
   at least 1% ascorbic palmitate;
   0.1% or less diazolidinyl urea;
   0.1% or less thretonate; and
   0.1% or less tetrasodium EDTA.

8. The composition of claim 7 wherein the combination of ascorbic acid and proanthocyanidine stimulates collagen synthesis.

9. The composition of claim 7 wherein the combination of ascorbic acid and proanthocyanidine provides sunscreen protection.

10. The composition of claim 7 wherein the water serves as a surfactant carrier of the composition into the dermal membrane of human skin.

11. The composition of claim 7 wherein the substances methylparaben, propylparaben, sodium hydroxide and tetrasodium EDTA serve as preservatives.

12. The composition of claim 7 wherein propylene glycol serves as a thickening agent; xanthum gum provides a buffer and pH adjuster; hyaluronic acid constitutes a lubricating agent; and thretonate enhances metabolite uptake of the composition.

13. The composition of claim 1 or claim 7 having superior free scavenger properties.

14. The composition of claim 1 or claim 7 for exfoliation of human skin without burning or irritating side effects or pain.

15. The composition of claim 1 or claim 7 wherein the combination of ingredients mitigates or eradicates hyperpigmentation.

16. The composition of claim 1 or claim 7 wherein the combination of ingredients mitigates or makes disappear wrinkles, improves firmness of skin by collagen synthesis, and in general improves the entire dermal membrane.

17. A method for application of the composition of claim 1 or claim 7 which comprises:

cleansing and defatting the skin thoroughly in the morning;

application of the respective composition to the skin immediately after cleansing and defatting; and application of a moisturizer to the skin immediately after applying the respective composition.

18. The method of claim 17 further including:

cleansing and defatting the skin thoroughly in the evening;

application of the respective composition to the skin immediately after said evening cleaning and defatting;

and application of a moisturizer to the skin in the evening immediately after applying the respective composition.

* * * * *